United States Patent [19]
Brune et al.

[11] Patent Number: 5,206,029
[45] Date of Patent: Apr. 27, 1993

[54] MEDICAMENT AND ITS PRODUCTION AND USE IN THE TREATMENT OF PAIN, INFLAMMATION AND FEVER IN MAN AND ANIMALS

[75] Inventors: Kay Brune, Marloffstein; Gerd Geisslinger, Nuremburg, both of Fed. Rep. of Germany

[73] Assignee: PAZ Arzneimittel-Entwicklungsgesellschaft mbH, Frankfurt, Fed. Rep. of Germany

[21] Appl. No.: 700,798

[22] Filed: May 16, 1991

[30] Foreign Application Priority Data

Sep. 12, 1990 [DE] Fed. Rep. of Germany ....... 4028906

[51] Int. Cl.$^5$ .......................... A61K 9/14; A61K 9/48; A61K 31/19
[52] U.S. Cl. ................. 424/489; 424/436; 424/456; 424/465; 514/570
[58] Field of Search ............... 424/465, 451, 436, 484, 424/456, 489

[56] References Cited

U.S. PATENT DOCUMENTS 3,784,705 1/1974 Adams et al. ........................ 424/317
4,209,638 6/1980 Nicholson et al. ................... 562/401

OTHER PUBLICATIONS

Caldwell et al., The Metabolic Chiral Inversion and Dispositional Enantio Selectivity of the 2-aryl Propionic Acids, 1988, Biochemical Pharmacology, vol. 37.
F. Jamali, Pharmacokinetics of Enantiomers of Chiral non-Steroidal anti-inflammatory Drugs, 1987, European Journal of Drug Metabolism . . . vol. 13.
Hutt et al., The Importance of Stereochemistry in the Chiral Pharmacokinetics of the 2 aryl propionic acids NSAIDS, 1984, Clinical Pharmco Kinetics, vol. 9.
Br. J. Clin. Pharmac. (1980), 10, 233S-235S. Gerald A. Higgs, Arachidonic Acid Metabolism, Pain and Hyperalgesia: . . . .
Nature New Biology vol. 231, Jun. 23, 1971, J. R. Vane, Inhibition of Prostaglandin Synthesis as a Mechanism of Action . . . .
Abstract No. A-4, Flurbiprofen. Flurbiprofen Dextrorotatroy Component (BTS 24332), and Placebo in Postepisiotomy Pain . . . .
Martindale, The Extra Pharmacopoeia, 29th Edition, 1989.

Primary Examiner—Thurman K. Page
Assistant Examiner—Neil Levy
Attorney, Agent, or Firm—Foley & Lardner

[57] ABSTRACT

The present invention provides a medicament for the treatment of painful and/or inflammatory diseases and/or of fever with flurbiprofen, wherein the previously separated enantiomers of flurbiprofen are worked up in a ratio of 99.5-0.5% to 0.5-99.5%, in combination with conventional pharmaceutical carriers and adjuvants, to give a medicament.

21 Claims, 2 Drawing Sheets

MEDICAMENT AND ITS PRODUCTION AND USE IN THE TREATMENT OF PAIN, INFLAMMATION AND FEVER IN MAN AND ANIMALS

BACKGROUND OF THE INVENTION

The present invention is concerned with flurbiprofen-containing medicaments comprising a mixture of flurbiprofen enantiomers, present as previously separated compounds, as active material, as well as with the preparation thereof, and with the use of said medicaments as rapidly or controlled inflowing, as well as acceleratedly-acting, analgesics and antiphlogistics and/or antipyretics in the case of pain and/or inflammations and/or fever in humans and animals.

Flurbiprofen (2-(2-fluoro-4-biphenylyl)propionic acid), which has the following structure:

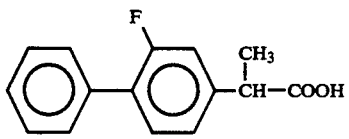

is a medicament which has been known for a long time (see Federal Republic of Germany Patent Specification DE-C-15 18 528) and which is widely used because of its anti-inflammatory, antipyretic and analgesic action (see Martindale, The Extra Pharmacopoeia, 20th edn., p. 18, 1989).

In the case of chemical synthesis, flurbiprofen is normally obtained as a racemate and is also used in this form in various medicaments. Furthermore, it is known that this compound, especially in the case of long-term treatment of painful and inflammatory processes, displays undesirable side effects, especially gastrointestinal irritations or damage, such as ulcers, perforations and the like (see Martindale (loc. cit.)).

It is known that, in the case of many pharmacologically-active 2-arylpropionic acid derivatives, the biological in vitro activity (prostaglandin synthesis inhibition, thrombocyte aggregation inhibition) of one of the enantiomers is greater than that of the other one, whereas the side effects, in many cases, are to be attributed to both enantiomers or even to the pharmacologically less active enantiomer. Thus, in Federal Republic of Germany Patent Specification No. DE-A-29 09 794 a process is suggested to increase the proportion of the pharmacologically-active enantiomer in comparison with the racemate. For this purpose, a solution which contains the racemic active material or an active material already partly enriched in one of the enantiomers is reacted in a non-polar solvent with an optically active alkylamine, preferably with α-phenylethylamine, to give a diastereomeric salt mixture, the amount of solvent thereby not being sufficient in order to dissolve this salt completely. Therefore, the sparingly soluble component is enriched in the precipitate. Depending upon the optically-active base used and the solvent employed, in this way, inter alia, there can also be prepared the two optically-active enantiomers of flurbiprofen. However, the pharmacological effectiveness of the enantiomers is not given in this literature reference.

From A. Sunshine et al., Clin. Pharmacol Ther., 41 (2), 162/1987, it is known to use S(+)-flurbiprofen as an analgesic in the case of post-episiotomy pain. In a double blind study, it was thereby found that S(+)-flurbiprofen, compared with the racemate, is already more effective at half dosage so that it was assumed that the enantiomer is solely responsible for the analgesic action.

Surprisingly, we have now found that, contrary to this knowledge, not S(+)-flurbiprofen but also R(−)-flurbiprofen is outstandingly analgesically effective in recognized pain models. This unexpected result was verified by investigations in two animal models (mouse and rat). Not only in the cramp pain test in mice but also in the interleukin 1-induced pain test in rats, the R-enantiomer, as can be seen from FIGS. 1 and 2 of the accompanying drawings, is equal or even more effective by about one third to a half. Otherwise than in the case of other known 2-arylpropionic acid derivatives, these results are clearly to be assigned to the enantiomers, since not only after R(-) but also after S(+)-flurbiprofen administration, no or only a very small inversion takes place.

Furthermore, contrary to the published state of knowledge (v. supra), S(+)-flurbiprofen in the case of administration after episiotomy is preferably effective antiphlogistically and not preferably analgesically. This further surprising test result was tested on two inflammation models selected independently of one another. Thus, on macrophages (peritoneum of the mouse), it was shown that S(+)-flurbiprofen inhibits the liberation of prostaglandin more markedly than the R(−)-form.

In the case of carrageenin paw oedema in the rat, S(+)-flurbiprofen is also superior in its inflammation-inhibiting action to the R(−)-form, as is demonstrated in FIGS. 3 and 4 of the accompanying drawings. In accordance with the present thinking as seen from FIG. 7, we have found that only S(+)-flurbiprofen caused damage of the gastro-intenstinal mucosa of rats.

According to the present state of knowledge of the mechanism of action of medicaments in the case of successful combating of pain of differing genesis, differention must be made as follows.

In the case of analgesics, the rapid commencement of action is an outstanding factor. It is a prerequisite of this that, in the case of oral, topical or other non-parenteral forms of administration, an accelerated liberation initially takes place as well as a sufficiently good bioavailability of the active material(s). Furthermore, such analgesics block because the conduction from the awareness of pain takes place via a conduction system ascending from the periphery to the central nervous system (CNS), the control mechanisms being present on different planes of the CNS on which participate receptors with chiral structures.

Furthermore, it is assumed that the inhibition of the prostaglandin biosynthesis acts a a common feature of the action mechanism in the case of analgesics and antiphlogistics (see J. R. Vane, Nature, p. 231 et seq., 1971; G. A. Higgs, Brit. J. Clin. Pharmacol., 10, 233 et seq. 1980). Thus, this action is to be understood as a connecting member between the alleviation of pain and the inhibition of inflammation. However, all effects cannot be solely explained with this mechanism. Thus, in the case of acidic analgesics and/or antiphlogistics, such as flurbiprofen, neuro-physiological effects are also probable as a result of the incorporation of such active materials in the cell membranes.

Prostaglandins participate in the initiation of the classical symptoms in the case of inflammations, such as reddening, swelling, oedema and thus pain. Such inflammatory changes can be reduced by means of inflammation-inhibiting active materials, the patient thereby simultaneously experiencing an amelioration of pain. At present, this is the main field of use of the non-steroidal inflammation inhibitors (antiphlogistics). Of the antiphlogistics, only a few representatives can be employed for differentiated or pure treatment of pain. These include, for example, indomethacine, naproxen and ibuprofen, which are also analgesically effective in the case of spasms of the smooth musculature. By far the greater number of the non-steroidal antiphlogistics is excluded from anti-rheumatic therapy because of insufficient analgesic action and because of a number of undesirable effects.

SUMMARY OF THE INVENTION

Accordingly, it is an object of the present invention to provide a readily administrable and problem-free, parenterally administrable medicament which is effective in the case of pain and/or inflammation, and which possesses the smallest possible side effect quotient.

Another object of the present invention is to provide a medicament that is simple to prepare, flows in rapidly and controllably, is characterized by a good bioavailability and is adaptable in the case of diseases with differing analgesic and/or antiphlogistic requirements by simple variation to the frequently occurring disease manifestation.

Yet another object of the present invention is to provide an improved method for producing the foregoing medicament.

Still another object of the present invention is to provide a method for treating a human or animal patient suffering from a disease characterized by pain or inflammation.

In accomplishing the foregoing objectives, there has been provided, in accordance with one aspect of the present invention, a medicament effective for the treatment of a disease characterized by pain or inflammation, which comprises a mixture of the previously-separated R(−) and S(+) enantiomers of flurbiprofen and a pharmaceutically acceptable carrier, wherein the ratio of said R(−) and S(+) enantiomers of flurbiprofen is from about 99.5:0.5% to 0.5:99.5%.

In accordance with another aspect of the present invention there is provided a method for producing a medicament effective for the treatment of a disease characterized by pain or inflammation, which comprises the steps of providing substantially pure R(−) and S(+) enantiomers of flurbiprofen, combining said R(−) and S(+) enantiomers of flurbiprofen in a ratio from about 99.5:0.5% to 0.5:99.5% to form a mixture, and combining said mixture with a pharmaceutically acceptable carrier.

In accordance with a further aspect of the present invention there is provided a method for treating a human or animal patient suffering from a disease characterized by pain, comprising the step of administering to the patient a medicament as described above comprising an analgesically effective amount of a mixture of 50 to 99.5% R(−)-flurbiprofen and 50 to 0.5% S(+)-flurbiprofen.

In accordance with still a further aspect of the present invention there is provided a method for treating a human or animal patient suffering from a disease characterized by inflammation, comprising the step of administering to the patient a medicament as described above comprising an antiphlogistically effective amount of a mixture of 50 to 99.5% S(+)-flurbiprofen and about 0.5 to 50% R(−)-flurbiprofen.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The invention may be more readily understood by referring to the accompanying drawings by which

DETAILED DESCRIPTION OF THE PREFERRED EMBODIMENTS

According to the present invention, there is provided a medicament for the treatment of painful and/or inflammatory diseases with flurbiprofen, wherein the previously separated enantiomers of flurbiprofen are worked up in a ratio from about 99.5–0.5% to 0.5–99.5%, in combination with conventional pharmaceutical carriers and adjuvants, to give a medicament.

According to the present invention, the pure enantiomers are either isolated in a known manner from flurbiprofen racemate by resolution or are stereospecifically synthesized. Thereafter, the enantiomers are worked up in a ratio adapted to the particular case of use, together with appropriate, pharmacologically compatible adjuvant and carrier materials, to give the medicaments according to the present invention.

Surprisingly, we have found that the enantiomers previously separated according to the present invention and then mixed together again in the desired mixing ratio in the final medicament display a substantially quicker liberation of the active material than the racemate. This finding is important for therapeutic use since the quicker liberation of active material also results in a correspondingly quicker inflow of the active material into the body, which is extremely important especially in the case of analgesics.

Figure 5:
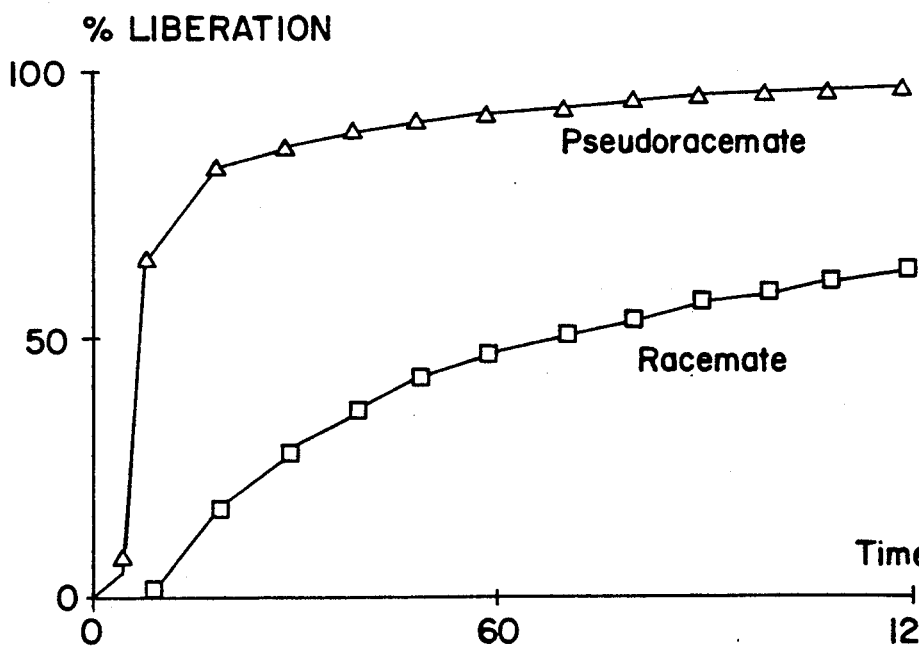
FIG. 5 is a graph showing the speed of dissolving for a racemate and pseudoracemate (i.e., mixture of previously-separated enantiomers) of flurbiprofen.

The speed of dissolving was thereby determined according to the procedure of U.S.P XXII, p. 683, for ibuprofen tablets (0.9 phosphate buffer, pH 7.2, speed of stirring 150 r.p.m., concentration determination by UV absorption measurement at 220 nm, determination via 10 tablets). Use was made of flurbiprofen tablets containing 100 mg. of active material according to the following Examples. The results are given in the graph shown in FIG. 5 of the accompanying drawings.

Known, undesired side effects, for example gastrointestinal complaints, are, in the case of nonsteroidal inflammation inhibitors, substantially coupled with the mechanism of action. In medical practice, these are taken into account in the case of administration in diseases of the rheumatic type. However, in the case of patients who primarily require an amelioration of pain, the quotient of undesired effects should be minimal. According to the present invention, in the case of the administration of flurbiprofen, this can be achieved by increasing the proportion of R(−)-flurbiprofen in the enantiomer combination or by administering R(−)-flurbiprofen in pure form since, as stated above, R(−)-flurbiprofen has a stronger pain-ameliorating action in acute cases and, on the other hand, also manifests a lower grade toxicity on the gastrointestinal tract than the racemate or the S(+)-enantiomer.

Medicaments with flurbiprofen are usually administered to humans and animals in the form of tablets, dragees, powders, granulates or suppositories, as well as parenterally, as sterile solutions, or orally as non-sterile solutions or suspensions. Usually, a rapid commencement of action is desired. However, forms of administration with delayed liberation can also be prepared by means of which a longer-lasting action is ensured. In such cases, the R(−)-enantiomer can be present in rapidly inflowing form and the S(+)-enantiomer in retarded form. Such forms of administration with a delayed liberation are preferably those which are first liberated in the distal section of the intestine, for example in the colon, i.e. after administration, liberation is delayed but is then spontaneous. Such an "evening before pill" can be given in the evening to a patient with rheumatic complaints, such as morning stiffness, in order, according to the present invention, to wake up the next morning free of complaints. The known formulations for racemic flurbiprofen can also be used directly, without further changes, for the enantiomeric mixture according to the present invention.

Especially preferred is an oral administration in the form of tablets, dragees or capsules or possibly also in the form of chewable tablets or chewable masses, the powdered active materials with appropriate particle distribution thereby being mixed in the usual manner with known pharmaceutically compatible adjuvant and carrier materials and further pressed to give tablets or dragees or filled into gelatine capsules.

The flurbiprofen enantiomers are contained in the medicaments according to the present invention in a mixing ratio from about 99.5:0.5 to 0.5:99.5% and preferably from about 95:5 to 5:95%. Depending upon the form of administration, the active material thereby accounts for about 2 to 60% of the formulation.

For the treatment of pain or of chronic diseases with predominant pain, the medicament according to the present invention can contain about 50 to 99.5% and preferably about 60 to 95% of R(−)-flurbiprofen, whereas for the treatment of inflammation or of diseases with predominant inflammation, the medicament according to the present invention can contain about 50 to 99.5% and preferably about 60 to 95% of S(+)-flurbiprofen.

Solid forms of administration contain about 20 to 80% of filling materials. As such, there can be used, inter alia, starch, lactose, glucose, mannitol, calcium carbonate, calcium phosphate, cellulose and other substances known for this purpose. In order to accelerate the liberation and thus to improve the availability, a release agent can be added to the formulation in an amount from about 2 to 10%. As release agent, carboxymethyl starch, carboxymethyl cellulose, polyvinylpyrrolidone and silica gel have proved to be especially useful. Furthermore, the formulation can also contain lubricants in an amount from about 0 to 5%, in which case talc, magnesium stearate or calcium stearate and other adjuvants with lubricating properties can be added to the powder in order to simplify the working up.

The powders are usually mixed dry and subsequently moist granulated with a conventional binding agent, for example starch paste or also water, and then dried. Subsequently, the granulate can then be pressed into tablets, possibly with the addition of further lubricants, or can be filled into capsules. It is advantageous subsequently to dragee the tablets with a sugar coating or to lacquer them with a soluble film former. For the improvement of administration, this coating can also contain flavoring and sweetening materials. Besides the coating agents conventional in pharmaceutical techniques (sugars, such as saccharose or lactose, various types of cellulose, such as methyl cellulose or cellulose acetate phthalate, polyacrylates, or polyvinyl acetate phthalate), carnauba wax can preferably be used as polishing agent.

Filling into capsules can take place either as dry powder or as granulate or pellets or as suspension in a vegetable oil or other pharmaceutically compatible liquid carrier material. The active materials, which are relatively sparingly soluble in water, can also be suspended in water in the presence of an appropriate suspension agent, such as tragacanth, methyl cellulose or the like.

Also known is the use of the flurbiprofen active materials in the form of suppositories for rectal or vaginal administration, in which case, besides the active material, fats or polyglycols can be used as carrier materials, the melting points of which either lie in the body temperature range or which dissolve after administration.

Furthermore, the speed of dissolving can also be changed in that, instead of flurbiprofen, there are also used salts thereof, alkali metal, alkaline earth metal, ammonium or amino acid salts which are water soluble thereby being preferred. Complex salts with basic amino acids can be used directly and mixed salts with neutral or acidic amino acids are previously converted into the alkali metal, alkaline earth metal or ammonium salts. A preferred amino acid is lysine. Other methods also known for medicaments, in which the active material is adsorbed onto aluminum oxide gels, can also be carried out with the flurbiprofens according to the present invention. The flurbiprofen salts produced can then be further worked up in the manner described hereinbefore. Preferably, the flurbiprofen salts are prepared indirectly by adding the bases required for the salt formation to the binding agent solution serving for the granulation so that the corresponding salts are formed during the granulation process.

For the treatment of pain with the flurbiprofen medicaments according to the present invention, there are required about 0.25 to 5 mg. of active material per kg. of body weight, which can be taken, for example, in 2 to 5 portions divided up over the day. Retard forms are especially used in order to reduce the administration to 1 or 2 dosages. Therefore, an individual dose should contain from 10 to 100 mg. of active material.

Pharmacological Experiments

Analgesic Action in the Writhing Test (cf. Domer, Animal Exp. in Pharm. Analysis, 1971, p. 312)

Figure 6:
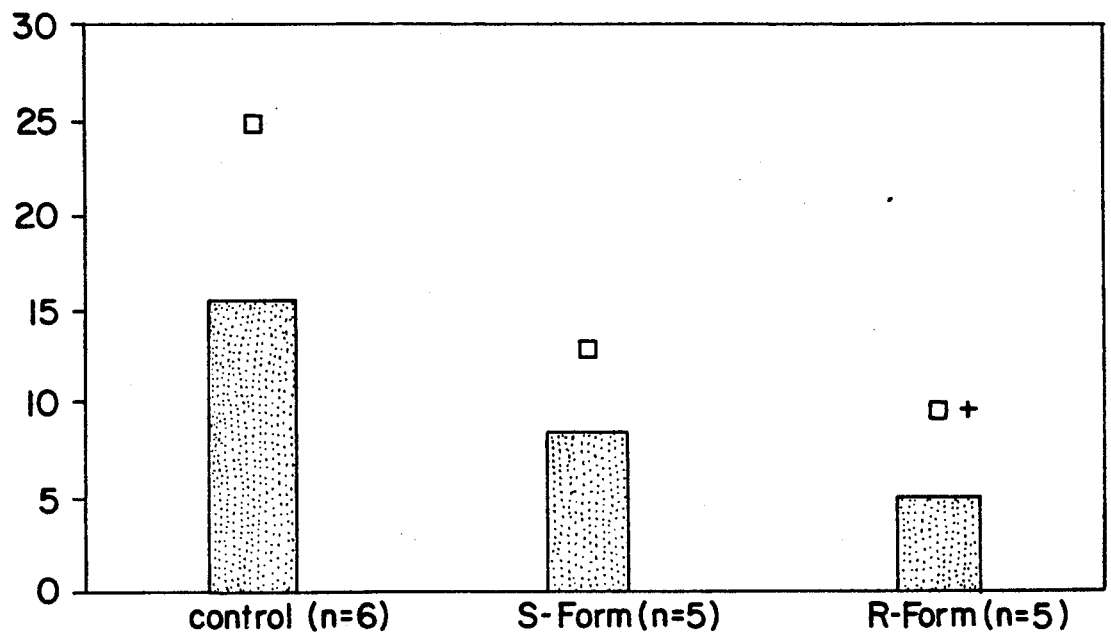
FIG. 6 is a plot of a writhing test in mice using the flurbiprofen enantiomers.

Equal numbers of male and female NMRI mice (defined strain) with an average body weight of about 20 g. have administered thereto, per dosage group, either 1.0 mg. S(+)- or 1.0 mg. R(−)-flurbiprofen per os per kg. body weight or an adequate amount of placebo (N=6). About 30 minutes after administration of the test preparations, the experimental animals are given an intraperitoneal injection of an aqueous solution of acetic acid in conventional concentration. There is observed the appearance or the non-appearance of typical writhing movements in the sequential process during a period of observation of 30 minutes. The results are given in FIG. 6 of the accompanying drawings, in which the number of writhing movements is plotted on the ordinate. In comparison with the control, the result is significant in the case of the administration of the R(−)-enantiomer ($p<0.05$ two-sided unpaired Student's test).

Action on Carrageenin-induced Paw Oedema of the Rat (cf. Domer, Animal Exp. in Pharm. Analysis, 1971, p. 303).

Figure 1:
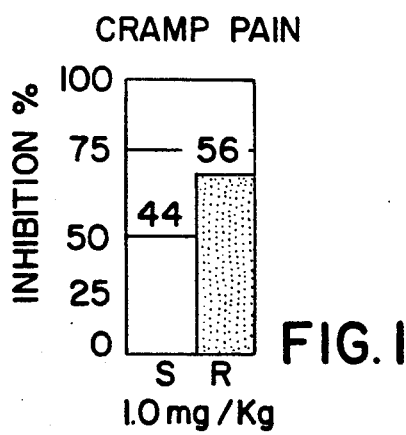
FIGS. 1–4 are graphs of tests in rats for cramp pain, interleukin-1-induced pain, prostaglandin production and carrageenin-induced paw oedema for the R(−) and S(+) enantiomers of flurbiprofen.
Figure 2:
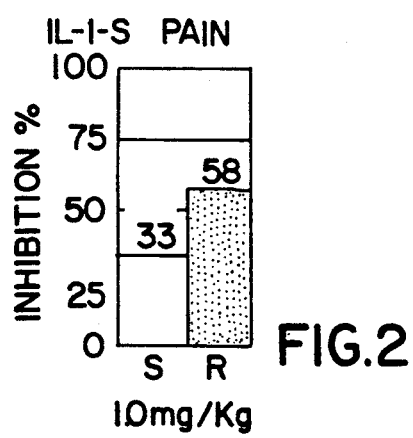
Figure 3:
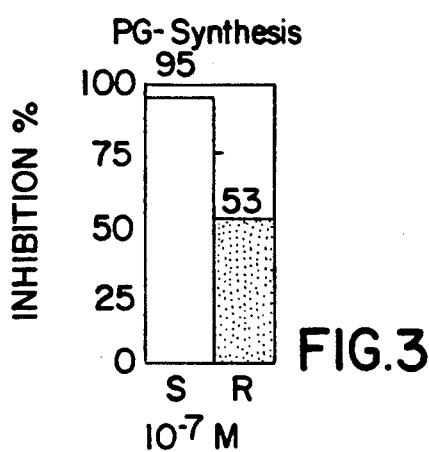
Figure 4:
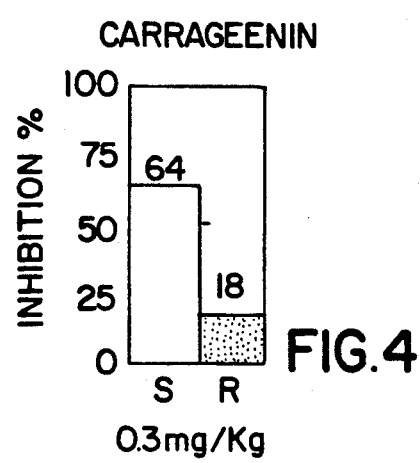

To male Sprague-Dawley rats, each with a body weight of 120 to 150 g., were administered per os with a stomach probe the test substances (0.3 mg./kg. body weight). Immediately thereafter, into the left rear paw was injected subplantary 0.1 ml. of a .1% carrageenin solution in order to induce oedema. After 3 hours p.a., the paw volumes were determined by means of a plethysmometer (modified method according to Hofrichter). By means of S(+)-flurbiprofen, the oedema was inhibited by 64%, whereas by R(−)-flurbiprofen the oedema was only inhibited by 18% (cf. FIG. 4 of the accompanying drawings).

Gastrointestinal Toxicity in the Rat (cf. Beck et al., Arch. Toxicology, 1990, pp. 210-217)

Figure 7:
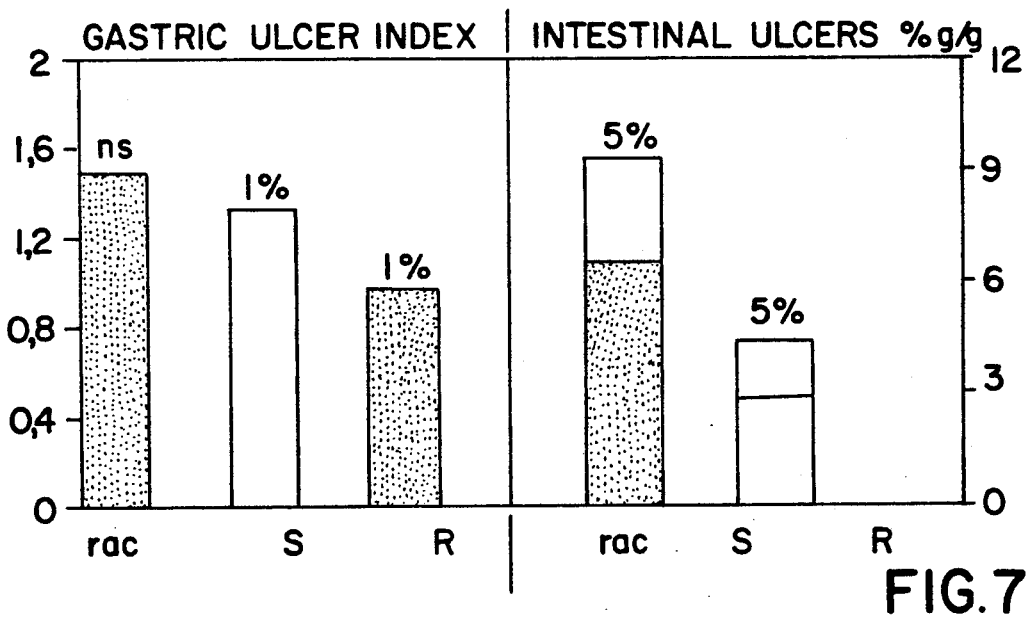
FIG. 7 is a plot of intestinal lesion occurrence in rats using the flurbiprofen enantiomers.

R(−)-Flurbiprofen causes distinctly less gastric ulcerations after oral administration of 25 mg. of test substance per kg. of body weight on the investigated fasting rat collective (N=9) than S(+)- or racemic flurbiprofen. No lesions were observed in the small intestine after oral administration of 25 mg. R(−) enantiomer per kg. of body weight after the taking of food, as can be seen from the results given in FIG. 7 of the accompanying drawings.

Each of the test groups were sacrificed after 24 hours, the stomach and intestines were removed and the stomach opened and cleaned with salt solution. The number of ulcerations multiplied with the diameter thereof in mm. is given as the "gastric ulcer index". The unopened small intestine was investigated for white and brown color changes. The corresponding sections were cut out and the weight thereof in comparison with the total weight plotted in % as "intestinal ulcer". The results are significant in the t-test in comparison with the control.

Medicinal Compositions

Tablets

1000 Tablets each with a content of 100 mg. flurbiprofen as pseudoracemate were produced as follows:

| | |
|---|---|
| R(−)-flurbiprofen | 50 g. |
| S(+)-flurbiprofen | 50 g. |
| lactose | 75 g. |
| maize starch | 50 g. |
| magnesium stearate | 4 g. |
| silicon dioxide | 5 g. |

The enantiomers are finely ground (air jet mill), mixed with the adjuvant materials and pre-compressed. A granulate is produced therefrom in known manner and pressed into tablets with a weight of about 235 mg.

With reference to this production procedure, there can also be produced tablets with other enantiomer proportions per tablet in the ratio according to the present invention. Furthermore, on the basis of this composition, tablets can also be produced with, for example, a proportion of total active materials of 25 or 50 mg.

Injection Solution

A sterile aqueous solution for parenteral administration, which contains per liter 350 mg. of the enantiomer mixture, is prepared as follows, for example as the sodium salt:

| | |
|---|---|
| R(−)-flurbiprofen, sodium salt[+] | 266 mg. |
| S(+)-flurbiprofen, sodium salt[+] | 87 mg. |
| water p.i.; q.s. | 1000 ml. |

[+] = 99.5% purity

Instead of the sodium salts, other salts can also be used which are obtained after neutralization of the enantiomer-pure active materials with, for example, ammonia, amino acids, such as lysine or the like, and having regard to the equivalent weights in question. The solutions are filtered into sterile containers which are then sealed.

Hard Gelatine Capsules

About 1000 hard gelatine capsules for oral administration, each containing 50 mg. R(−)-flurbiprofen, are produced as follows:

| | |
|---|---|
| R(−)-flurbiprofen (99.5:pure) | 50 g. |
| lactose | 100 g. |
| maize starch | 20 g. |
| talc | 20 g. |
| magnesium stearate | 2 g. |

The finely ground R(−)-flurbiprofen is homogeneously mixed with the other ingredients and filled in known manner into capsules. In an analogous manner, there can be produced capsules containing 25 mg., 75 mg. or 100 mg. R(−)-flurbiprofen or also with flurbiprofen enantiomer mixtures in the ratios to be used according to the present invention.

Suspension for Oral Administration

In order to produce 1000 ml. of an aqueous suspension, an oral dosage unit (1 teaspoon=5 ml.) of which contains 5 mg. R(−)-flurbiprofen, as well as 95 mg. S(+)-flurbiprofen, as aluminum salts, the following composition is used:

| | |
|---|---|
| R(−)-flurbiprofen | 1 g. |
| S(+)-flurbiprofen | 19 g. |
| citric acid | 2 g. |
| benzoic acid | 1 g. |
| sugar | 700 g. |
| tragacanth | 5 g. |
| lemon oil | 2 g. |
| desalinated water, q.s. | 1000 ml. |

The citric acid, benzoic acid, sugar, tragacanth and lemon oil are first suspended with sufficient water to give about 800 to 900 ml. of suspension. Thereafter, the micronised flurbiprofen enantiomers are homogeneously stirred in and the mixture made up to 1000 ml. with water.

Suppositories

A suppository which, as active material, can contain 10 to 100 mg, of the enantiomer mixture and has a weight of about 2 g., has the following composition:

| | |
|---|---|
| R(−)-flurbiprofen | 90 mg. |
| S(+)-flurbiprofen | 10 mg. |
| hard fat | 1890 mg. |
| tocopherol | 10 mg. |

If the amount of active material(s) is to be reduced, the amount of hard fat is to be increased correspondingly.

Cream

The preparation of a cream containing 4% of flurbiprofen enantiomers is carried out in known manner, the following components thereby giving a typical formulation:

| | |
|---|---|
| R(−)-flurbiprofen | 1.0 g. |
| S(+)-flurbiprofen | 3.0 g. |
| triglycerides, average chain length | 35.0 g. |
| glycerol monostearate-polyoxyethylene stearate mixture | 6.0 g. |
| polyoxyethylene fatty acid esters | 4.0 g. |
| propane-1,2-diol | 4.0 g. |
| sodium methyl 4-hydroxybenzoate | 0.1 g. |
| xanthan gum | 0.2 g. |
| desalinated water, q.s. | 100.0 g. |

The active materials are dissolved in the oily phase and heated to about 60° C. Thereafter, the aqueous phase, which is also preheated, is stirred in and uniformly further stirred until cool. A strand of about 2.5 cm. contains about 100 mg. of the active material mixture.

Film Tablets

Flurbiprofen Tablet Formulation 38.5 kg. of flurbiprofen lysinate are dry mixed with 7.5 kg. of microcrystalline cellulose, granulated with 3 kg. of gelatine (10% on water) and dried, then mixed with 0.5 kg. magnesium stearate, 1 kg. of talc and 2 kg. of sodium carboxymethylcellulose and pressed to give round tablets with a diameter of 6 mm. and a weight (residual moisture: 0.8–1.5%) of 260 mg. The finished tablets are coated with a lacquer coating from a solution containing 0.7% glycerol, 4% methyl cellulose, 0.7% polyglycol 6000, 58% water and 36.6% acetone and dried.

What is claimed is:

1. A medicament effective for the treatment of a disease characterized by pain or inflammation which comprises
   (a) a mixture of the previously-separated R(−) and S(+) enantiomers of flurbiprofen and
   (b) a pharmaceutically acceptable carrier, wherein the ratio of said R(−) and S(+) enantiomers of flurbiprofen is from about 99.5:0.5% to 0.5:99.5% wherein the medicament further comprises 2–10% of a release agent.

2. A medicament as claimed in claim further comprising an adjuvant.

3. A medicament as claimed in claim wherein said ratio is from about 95:5% to 5:95%.

4. A medicament as claimed in claim 1 which is effective for the treatment of pain or of chronic diseases with a predominant state of pain, wherein said ratio is from 99.5:0.5% to 50:50%.

5. A medicament as claimed in claim 4, wherein said ratio is from 95:5% to 60:40%.

6. A medicament as claimed in claim 1 which is effective for the treatment of inflammation or of diseases with predominant inflammation, wherein said ratio is from 50:50% to 0.5:99.5%.

7. A medicament as claimed in claim 6, wherein said ratio is from 40:60% to 5:95%.

8. A medicament as claimed in claim 1 in the form of a tablet, dragee, capsule, chewable mass, cream, suppository.

9. A medicament as claimed in claim 1, comprising 2 to 60 wt.% of the enantiomers based on the total weight of the medicament.

10. A medicament as claimed in claim 10, wherein said flurbiprofen enantiomers are in the form of flurbiprofen salts or aluminum compounds.

11. A medicament as claimed in claim 10, wherein said salts are selected from the group consisting of alkali metal, alkaline earth metal, ammonium and amino acid salts.

12. A medicament as claimed in claim 10, wherein said salts are lysinate salts.

13. A medicament as claimed in claim 1, further comprising a retarding additive or coating in an amount effective to delay the liberation of the enantiomers.

14. A medicament as claimed in claim 13, wherein said R(−)-enantiomer is present in rapidly inflowing form and said S(+)-enantiomer is present in retarded form wherein the retarded form does not contain a release agent.

15. A medicament according to claim 1 which is produced by a method which comprises the steps of:
   (a) providing substantially pure R(−) and S(+) enantiomers of flurbiprofen,
   (b) combining said R(−) and S(+) enantiomers of flurbiprofen in a ratio from about 99.5:0.5% to 0.5:99.5% to form a mixture, and
   (c) combining said mixture with a pharmaceutically acceptable carrier.

16. A medicament as claimed in claim 15, wherein step (a) comprises isolating said R(−) and S(+) enantiomers of flurbiprofen from flurbiprofen racemate.

17. A medicament as claimed in claim 15, wherein step (a) comprises stereospecifically synthesizing said R(−) and S(+) enantiomers of flurbiprofen.

18. A method for treating a human or animal patient suffering from a disease characterized by pain, comprising the step of administering to said patient a medicament comprising (a) an analgesically effective amount of a mixture of the previously separated R(−) and S(+) enantiomers of flurbiprofen, and mixture containing 50 to 99.5% R(−)-flurbiprofen and 50 to 0.5% S(+)-flurbiprofen and (b) a pharmaceutically acceptable carrier wherein the medicament further comprises 2–10% of a release agent.

19. A method as claimed in claim 18, wherein said mixture contains 60 to 95% R(−)-flurbiprofen and 40 to 5% S(+)-flurbiprofen.

20. A method for treating a human or animal patient suffering from a disease characterized by inflammation, comprising the step of administering to said patient a medicament comprising (a) an antiphlogistically effective amount of a mixture of the previously separated R(−) and S(+) enantiomers of flurbiprofen, said mixture containing 50 to 99.5% S(+)-flurbiprofen and 50 to 0.5% R(−)-flurbiprofen and (b) a pharmaceutically acceptable carrier wherein the medicament further comprises 2–10% of a release agent.

21. A method as claimed in claim 20, wherein said mixture contains 60 to 95% S(+)-flurbiprofen and 40 to 5% R(−)-flurbiprofen.

* * * * *